United States Patent
Schoenberg

(10) Patent No.: US 10,360,649 B2
(45) Date of Patent: Jul. 23, 2019

(54) AUTOMATED DATA ENTRY METHOD AND SYSTEM

(75) Inventor: Roy Schoenberg, Boston, MA (US)

(73) Assignee: Cognizant TriZetto Software Group, Inc., Englewood, CO (US)

( * ) Notice: Subject to any disclaimer, the term of this patent is extended or adjusted under 35 U.S.C. 154(b) by 2911 days.

(21) Appl. No.: 10/824,705

(22) Filed: Apr. 15, 2004

(65) Prior Publication Data

US 2005/0234745 A1    Oct. 20, 2005

(51) Int. Cl.
  *G06Q 10/10* (2012.01)
  *G16H 10/60* (2018.01)
  *G06Q 50/24* (2012.01)
  *G06F 17/24* (2006.01)

(52) U.S. Cl.
  CPC .......... *G06Q 50/24* (2013.01); *G06F 17/243* (2013.01); *G06Q 10/10* (2013.01); *G16H 10/60* (2018.01)

(58) Field of Classification Search
  CPC .............................. G16H 10/60; G06Q 10/10
  See application file for complete search history.

(56) References Cited

U.S. PATENT DOCUMENTS

| | | | |
|---|---|---|---|
| 6,463,417 B1 | 10/2002 | Schoenberg | |
| 6,988,075 B1* | 1/2006 | Hacker | G06Q 10/10 705/3 |
| 7,076,436 B1* | 7/2006 | Ross, Jr. | G06Q 10/06316 705/3 |
| 2003/0091158 A1* | 5/2003 | Puchek et al. | 379/38 |
| 2003/0097573 A1* | 5/2003 | Wheeler | G06Q 20/4014 713/182 |
| 2004/0254816 A1* | 12/2004 | Myers | G06F 19/324 705/2 |
| 2005/0021369 A1* | 1/2005 | Cohen | G06Q 30/02 705/2 |
| 2005/0021519 A1* | 1/2005 | Ghouri | G06Q 30/02 |

* cited by examiner

*Primary Examiner* — Robert A Sorey
*Assistant Examiner* — Kristine K Rapillo
(74) *Attorney, Agent, or Firm* — Dawn-Marie Bey; Bey & Cotropia PLLC

(57) ABSTRACT

A data entry method includes, in a computer-based data record including a plurality of data fields, defining one or more data fields for which desired field data is to be acquired. A data source in possession of the desired field data is contacted, and the desired field data is received from the data source.

12 Claims, 7 Drawing Sheets

AUTOMATED DATA ENTRY METHOD AND SYSTEM

RELATED APPLICATIONS

The following U.S. patent is hereby incorporated by reference into the subject application as if set forth herein in full: (1) U.S. Pat. No. 6,463,417, entitled "Method of Distributing Health Information".

FIELD OF THE INVENTION

This invention relates to automated data entry and, more particularly, to automated data entry within a medical records management system

BACKGROUND

Traditionally, the medical records of a patient are paper-based medical records, in which each medical service provider (that provides medical services to the patient) maintains a separate medical record for that patient.

Often, when treating patients who have certain medical conditions, it is advisable to routinely monitor various variables of that patient's condition. Examples of these conditions include those patients who are overweight, diabetic, or have hypertension; and examples of these variables include body weight, blood glucose levels, and blood pressure (respectively). Further, when monitoring these variables, the patient's medical record should be updated to include these monitored variables.

Unfortunately, with paper-based medical records, the medical service provider would need to manually review the medical records of each of their patients to determine which patients have these conditions. Additionally, these patients would have to be manually contacted so that their paper-based medical records could be manually updated.

Currently, paper-based medical records are slowly being converted into electronic, centrally-located databases that are accessible by various medical service providers.

SUMMARY OF THE INVENTION

In one implementation, a data entry method includes, in a computer-based data record including a plurality of data fields, defining one or more data fields for which desired field data is to be acquired. A data source in possession of the desired field data is contacted, and the desired field data is received from the data source.

One or more of the following features may also be included. The computer-based data record may be updated to include the desired field data. The computer-based data record may be a medical record. The data source may be a patient and the medical record may define at least a portion of the medical history of the patient.

Contacting a data source may include authenticating the data source. Authenticating the data source may include requiring that the data source enter an electronic password, and receiving the electronic password. Authenticating the data source may include requiring that the data source speak a verbal password, and receiving the verbal password. Authenticating the data source may include requiring that the data source provide an authenticating digital certificate, and receiving the authenticating digital certificate.

Contacting a data source may include transmitting an email to the data source, and providing the data source with text-based instructions concerning the desired field data. Contacting a data source may include telephonically contacting the data source, and providing the data source with speech-based instructions concerning the desired field data.

The desired field data may concern a numeric range-based variable.

In another implementation, a data entry method includes, in a computer-based medical record including a plurality of data fields, defining one or more data fields for which desired field data is to be acquired. The medical record defines at least a portion of the medical history of a patient. The patient is telephonically contacted, and the desired field data is received from the patient. The computer-based medical record is updated to include the desired field data.

The above-described methods may also be implemented as a sequence of instructions executed by a processor.

The details of one or more implementations is set forth in the accompanying drawings and the description below. Other features and advantages will become apparent from the description, the drawings, and the claims.

DETAILED DESCRIPTION OF THE PREFERRED EMBODIMENTS

Figure 1:
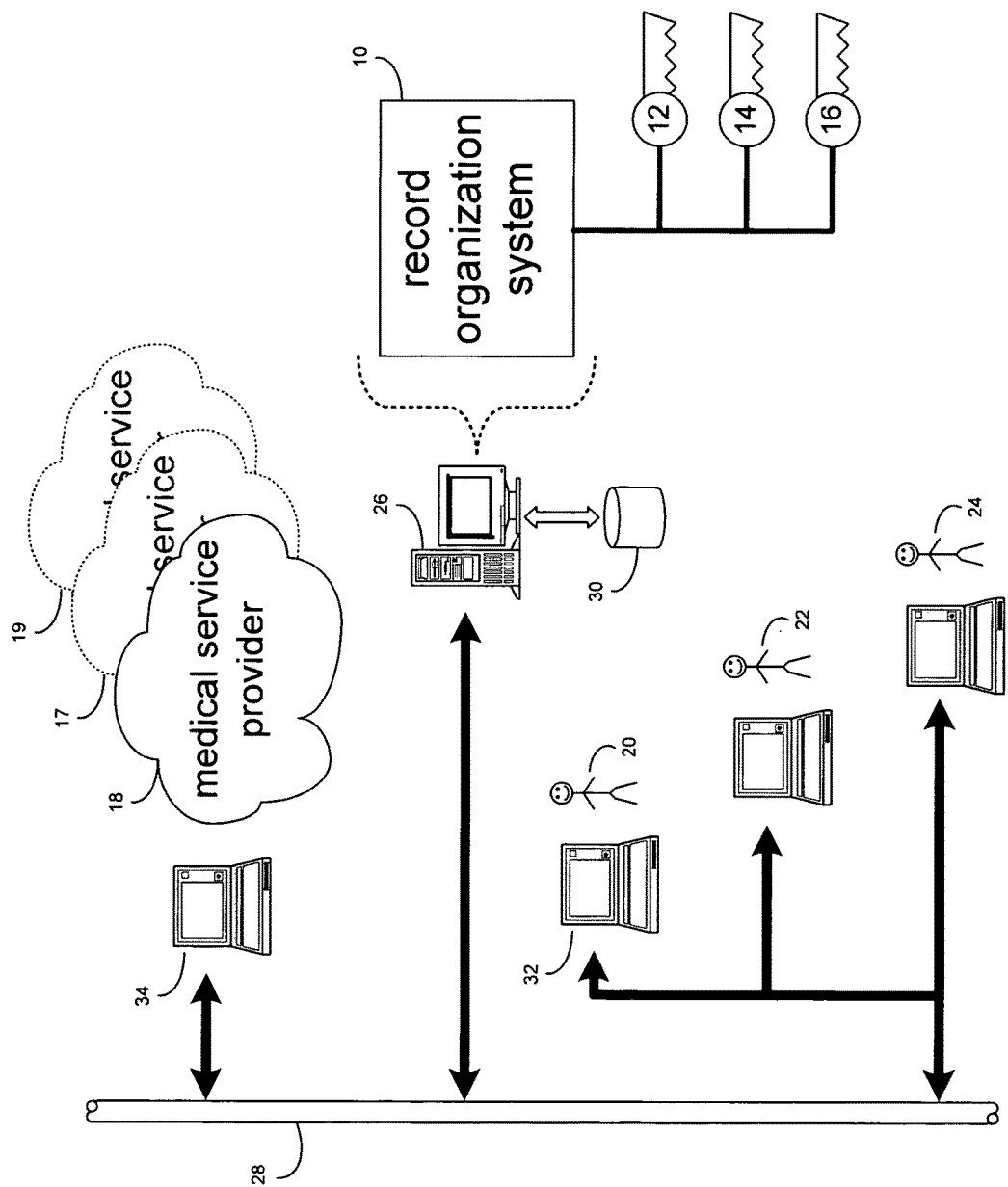
FIG. 1 is a diagrammatic view of record organization system coupled to a distributed computing network.

Referring to FIG. 1, there is shown a record organization system 10 that manages the various access keys 12, 14, 16 possessed by a medical service provider 18. Access keys 12, 14, 16 are provided to medical service provider 18 by various patients 20, 22, 24.

Record organization system 10 typically resides on and is executed by a computer 26 that is connected to network 28. Computer 26 may be a web server running a network operating system, such as Microsoft Window 2000 Server™, Novell Netware™, or Redhat Linux™. Typically, computer 26 also executes a web server application, such as Microsoft IIS™, Novell Webserver™, or Apache Webserver™, that allows for HTTP (i.e., HyperText Transfer Protocol) access to computer 26 via network 28.

The instruction sets and subroutines of record organization system 10, which are typically stored on a storage device 30 coupled to computer 26, are executed by one or more processors (not shown) and one or more memory architectures (not shown) incorporated into computer 26. Storage device 30 may be, for example, a hard disk drive, a tape drive, an optical drive, a RAID array, a random access memory (RAM), or a read-only memory (ROM).

As will be explained below in greater detail, a patient (e.g., patient 20) typically provides an access key (e.g., key 12) to medical service provider 18 through a patient computer 32, which is also connected to network 28. Additionally, medical service provider 18 accesses record organization system 10 through a client computer 34.

Figure 2:
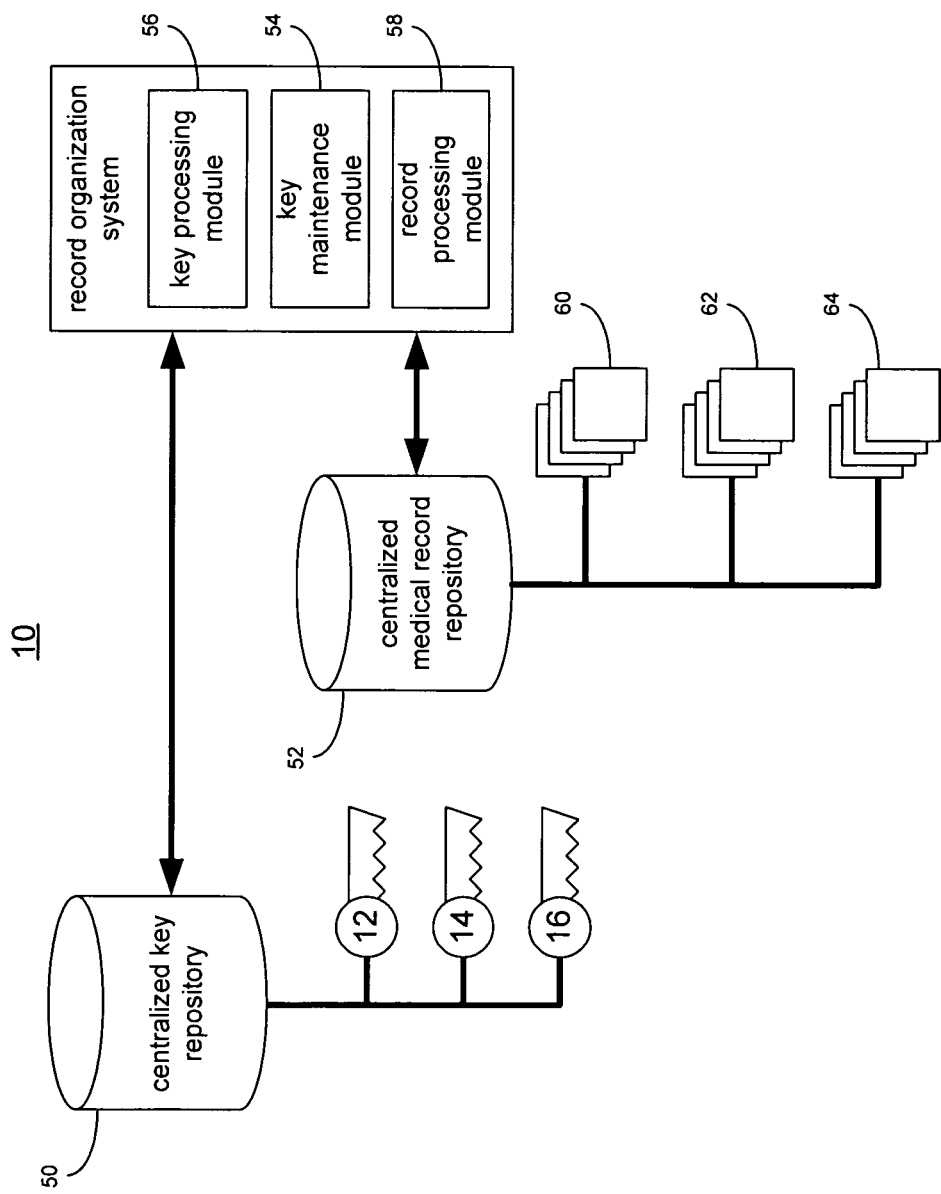
FIG. 2 is a more-detailed diagrammatic view of the record organization system of FIG. 1.

Referring also to FIG. 2, record organization system 10 includes a centralized key repository 50 and a centralized medical records repository 52. Additionally, record organization system 10 includes a key maintenance module 54, a key processing module 56, and a record processing module 58, each of which will be discussed below in greater detail.

Centralized medical records repository 52 allows for the centralized storage of medical records 60, 62, 64 concerning various patients 20, 22, 24 respectively. As disclosed in U.S. Pat. No. 6,463,417, medical records 60, 62, 64 are typically divided into portions or levels, in that certain portions are considered more confidential than other portions. For example, a portion/level of the medical record that may be considered the least confidential might include general patient identification information and information concerning the patient's blood type and allergies. A portion/level of a medical record that may be considered to have an intermediate level of confidentiality might include information concerning the serological data, psychiatric data, cardiology data, and genetic data. A portion/level of the medical record that may be considered highly confidential may include infectious disease (e.g., HIV, and sexually transmitted diseases) data.

This specific assignment of confidentiality levels and the apportionment of the medical record into various portions/levels is for illustrative purposes only and is not intended to limit the scope of this disclosure.

Medical records 60, 62, 64 may be incrementally generated/configured online by the various medical service providers that provide care to patients 20, 22, 24. Alternatively, existing medical records may be uploaded (i.e., transferred) to medical records repository 52 from a remote storage location (not shown).

Figure 3:
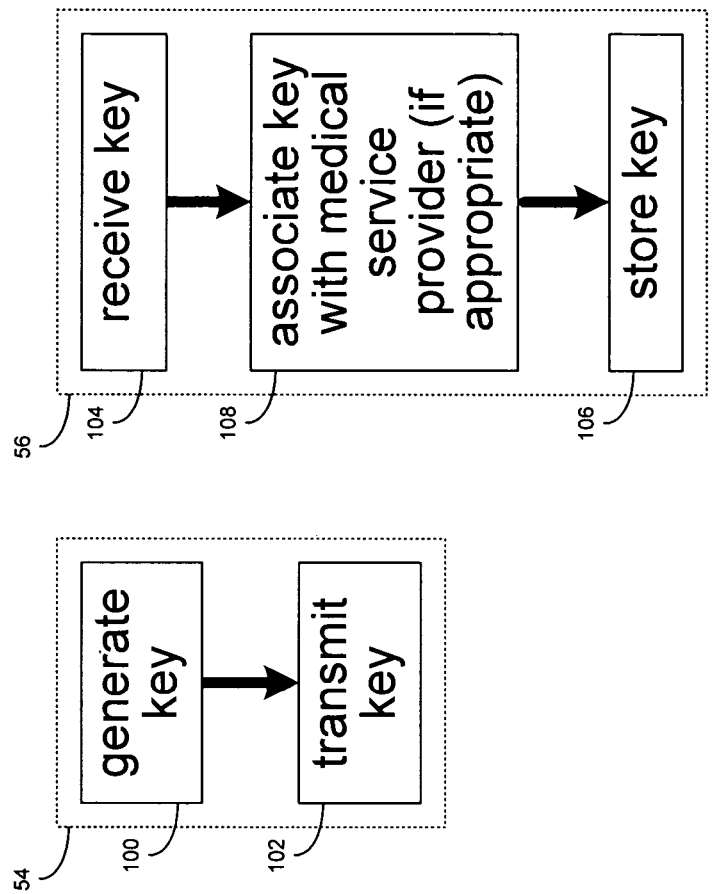
FIG. 3 is a diagrammatic view of a key maintenance module and a key processing module of the record organization system of FIG. 1.

Referring also to FIG. 3, patients 20, 22, 24 use key maintenance module 54 to generate 100 access keys 12, 14, 16 that grant access to various portions of the respective medical records 60, 62, 64. Accordingly, though the use of key maintenance module 54, the patient can generate access keys that not only regulate who has access to their medical records, but also regulate the level of access (i.e., which portions of a patient's medical record are viewable by the medical service provider to which the key is provided). Examples of access keys 12, 14, 16 are passwords (that allow access to various portions of a medical record) and decryption keys (that decrypt various portions of an encrypted medical record).

Typically, key maintenance module 54 is a web-enabled application that is accessed by the patients (e.g., patient 20) through a browser application (e.g., Microsoft Internet Explorer™, or Netscape Navigator™) that is running on patient computer 32, and the patient logs into record organization system 10 using an encrypted SSL (i.e., secure sockets layer) connection. Alternatively, key maintenance module 54 may be a local application that is executed locally on patient computer 32.

As stated above, key maintenance module 54 allows a patient to generate 100 an access key for a specific medical service provider that grants, to that medical service provider, a defined level of access to that patient's medical records. Once this access key is generated, the access key is transmitted 102 to the medical service provider 18. This transmission of the access key may be implemented by transferring the access key from the patient to the medical service provider. This may occur by attaching the access key to an email that is transmitted to the medical service provider. Once received, the medical service provider may then transfer the newly-generated key to the key processing module 56 (to be discussed below in greater detail) of the record organization system 10. Alternatively, the patient may directly transfer the newly-generated key to the key processing module 56 of the record organization system 10.

Regardless of the manner in which the patient transfers the access key to the medical service provider, the access key will ultimately be received 104 by key processing module 56, which receives any access keys (e.g., keys 12, 14, 16) generated and transmitted by patients 20, 22, 24. Once these keys are received 104, they are stored 106 on centralized key repository 50. Additionally, if record organization system 10 is servicing multiple medical service providers (e.g., medical service providers 17, 18, 19), the received keys are associated 108 with the appropriate medical service provider so that the keys transmitted to a first provider are not available to a second provider.

Figure 4:
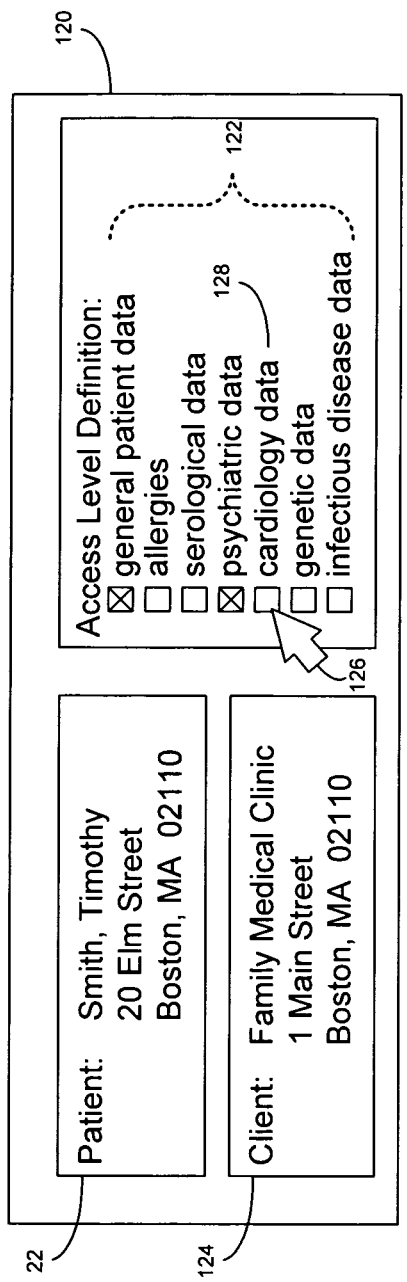
FIG. 4 is a diagrammatic view of a key configuration display screen rendered by the record organization system of FIG. 1.

Referring also to FIG. 4, when a patient is generating an access key (e.g., access key 14) for a medical service provider, key maintenance module 54 provides the patient (e.g., patient 22) with a rendered screen display 120 that allows the patient to select one or more access parameters 122 that define the access level granted to that particular medical service provider. Display 120 identifies the patient (i.e., Timothy Smith; patient 22) and allows the patient to select the recipient 124 of the access key being generated by the patient. In this example, the recipient 124 is Family Medical Clinic; i.e., medical service provider 18.

As stated above, medical records 60, 62, 64 are typically divided into portions or levels, such that certain portions are considered more confidential than other portions. The access parameters 122 selected (i.e., checked) by the patient define the various portions of the patient's medical record that the medical service provider is going to have access to. In this particular case, the access key being generated by patient Timothy Smith (i.e., patient 22) for the Family Medical Clinic (i.e., medical service provider 18) is going to allow the medical service provider to access only two portions of the patient's medical record, namely the general portion and the psychiatric data. As the remaining access parameters are unchecked, medical service provider 18 is going to be prohibited from accessing any other portion of the patient's medical record, such as cardiology data 128 in the illustrated example. When generating the access key, the patient selects the appropriate access parameters 122 using a mouse pointer 126 (or some other pointing device, not shown).

Figure 5:
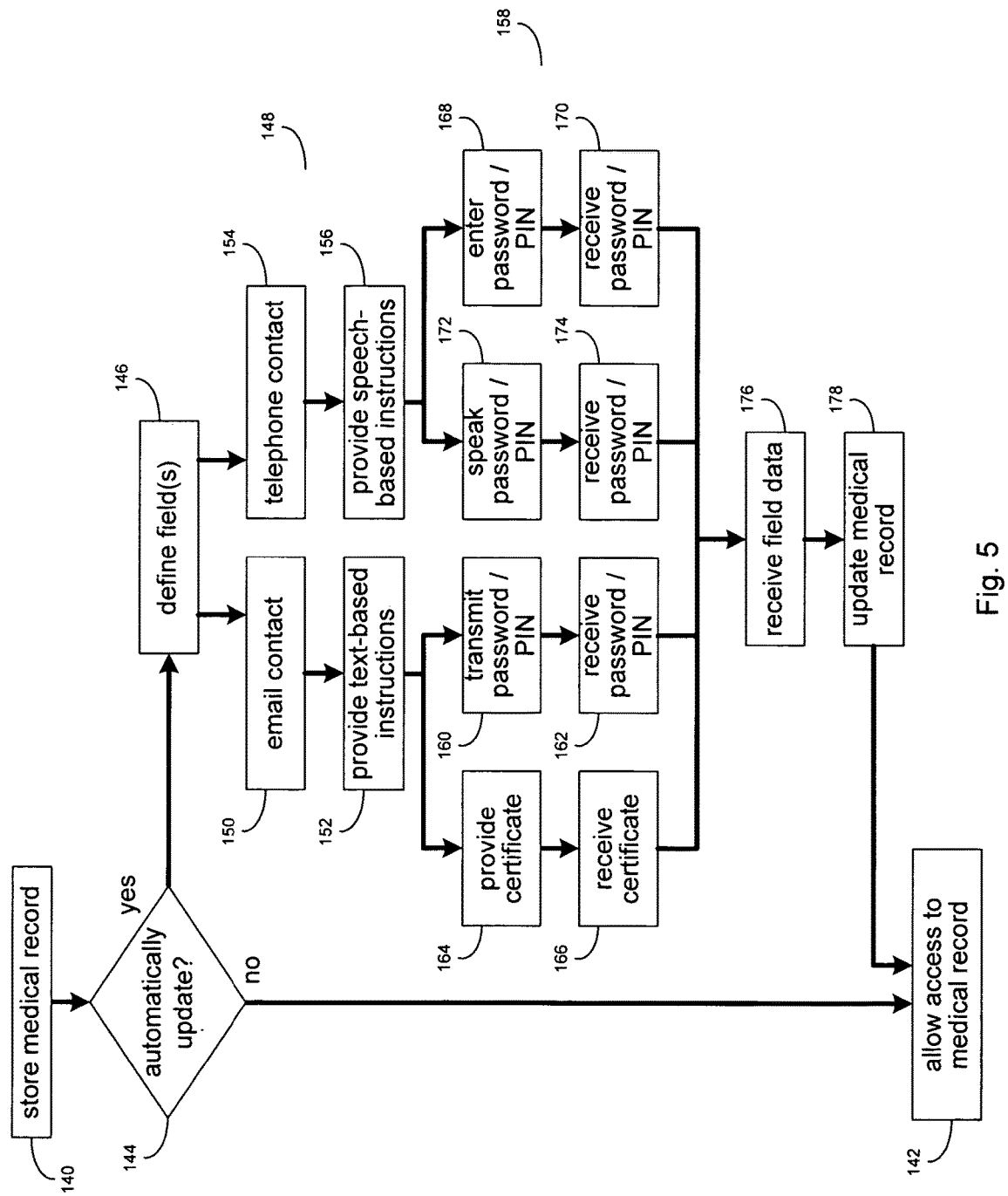
FIG. 5 is a block diagram of a record processing module of the record organization system of FIG. 1.

Referring also to FIG. 5, when medical records are initially received, initially generated, and/or edited, record processing module 58 stores 140 the medical record on centralized medical record repository 52. Typically, medical record repository 52 is a database that allows for the organized storage and retrieval of the medical records 60, 62, 64.

Once these medical records are stored on medical record repository 52, record processing module 58 allows the medical service provider 18 to access 142 the medical records 60, 62, 64 stored on medical records repository 52. However, the medical service provider 18 is only given access to the portions of the medical records for which the medical service provider 18 possesses the appropriate key. For example, assume that medical service provider 18 is a medical clinic that provides an array of medical services to its patients. Further, assume that patient 20 uses medical service provider 18 for all of their medical needs; patient 22 uses medical service provider 18 solely for treatment of depression; and patient 24 uses medical service provider 18 solely for treatment of HIV.

Concerning the access keys generated by each of these patients for medical service provider 18: patient 20 would typically provide medical service provider 18 with an access key (i.e., key 12) that grants access to their entire medical record; patient 22 would typically provide medical service provider 18 with an access key (i.e., key 14) that grants access to the general and psychiatric portions of their medical record; and patient 22 would typically provide medical service provider 18 with an access key (i.e., key 16) that grants access to the general and infectious disease portions of their medical record.

Record processing module 58 is typically a web-enabled application that is accessed by the medical service provider 18 through a browser application (e.g., Microsoft Internet Explorer™, or Netscape Navigator™) that is running on client computer 34. Typically, medical service provider 18 logs into record organization system 10 using an encrypted SSL (i.e., secure sockets layer) connection.

Figure 6:
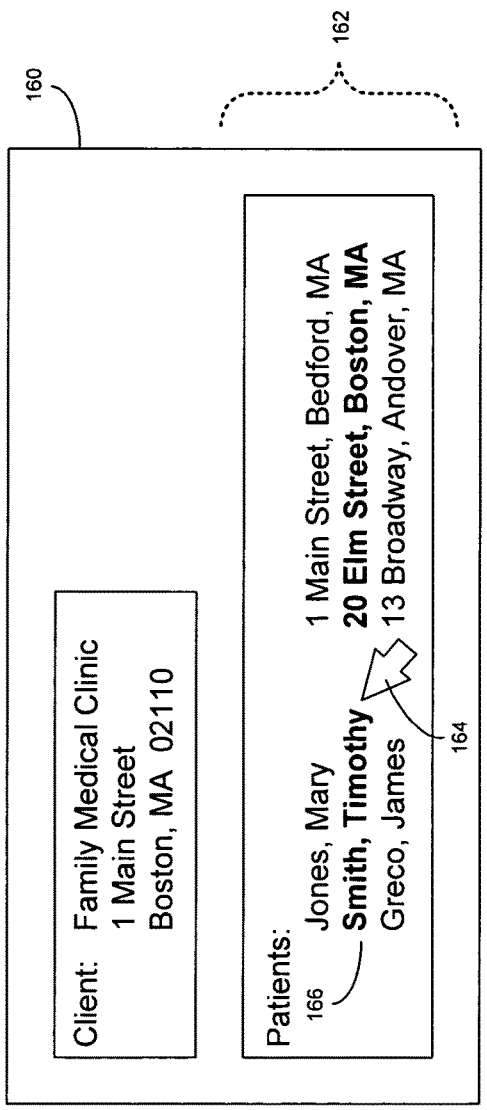
FIG. 6 is a diagrammatic view of a patient selection display screen rendered by the record organization system of FIG. 1.

Referring also to FIG. 6, when accessing record organization system 10, record processing module 58 provides the medical service provider 18 with a rendered screen display 160 that includes a list of patient identifiers 162. Patient identifiers 162 define the particular patient(s) who provided access keys to medical service provider 18 (i.e., granting medical service provider 18 access to various portions of their medical record(s)). The patient identifiers 162 may be any element that uniquely identifies the patient, such as the patient's name, the patient's social security number, or a unique patient number. In this particular example, Mary Jones is patient 20, Timothy Smith is patient 22 (as stated above), and James Greco is patient 24.

The presence of each of these names in the list of patient identifiers 162 indicates that a key was received from that patient. In order to access the medical record of a patient for which the medical service provider has an access key (i.e., for one of the patients listed in the list of patient identifiers 162), the medical service provider 18 selects the appropriate identifier using a mouse pointer 164 (or some other pointing device, not shown). For example, if the medical service provider wanted to access the medical record of Timothy Smith (i.e., patient 22), medical service provider 18 would typically double click (using a mouse) on the specific identifier 166 associated with Timothy Smith. Record processing module 58 would then, in turn, use access key 14 to access (i.e., retrieve, decrypt, and display) medical record 62, the medical record of Timothy Smith, i.e., patient 22.

Figure 7:
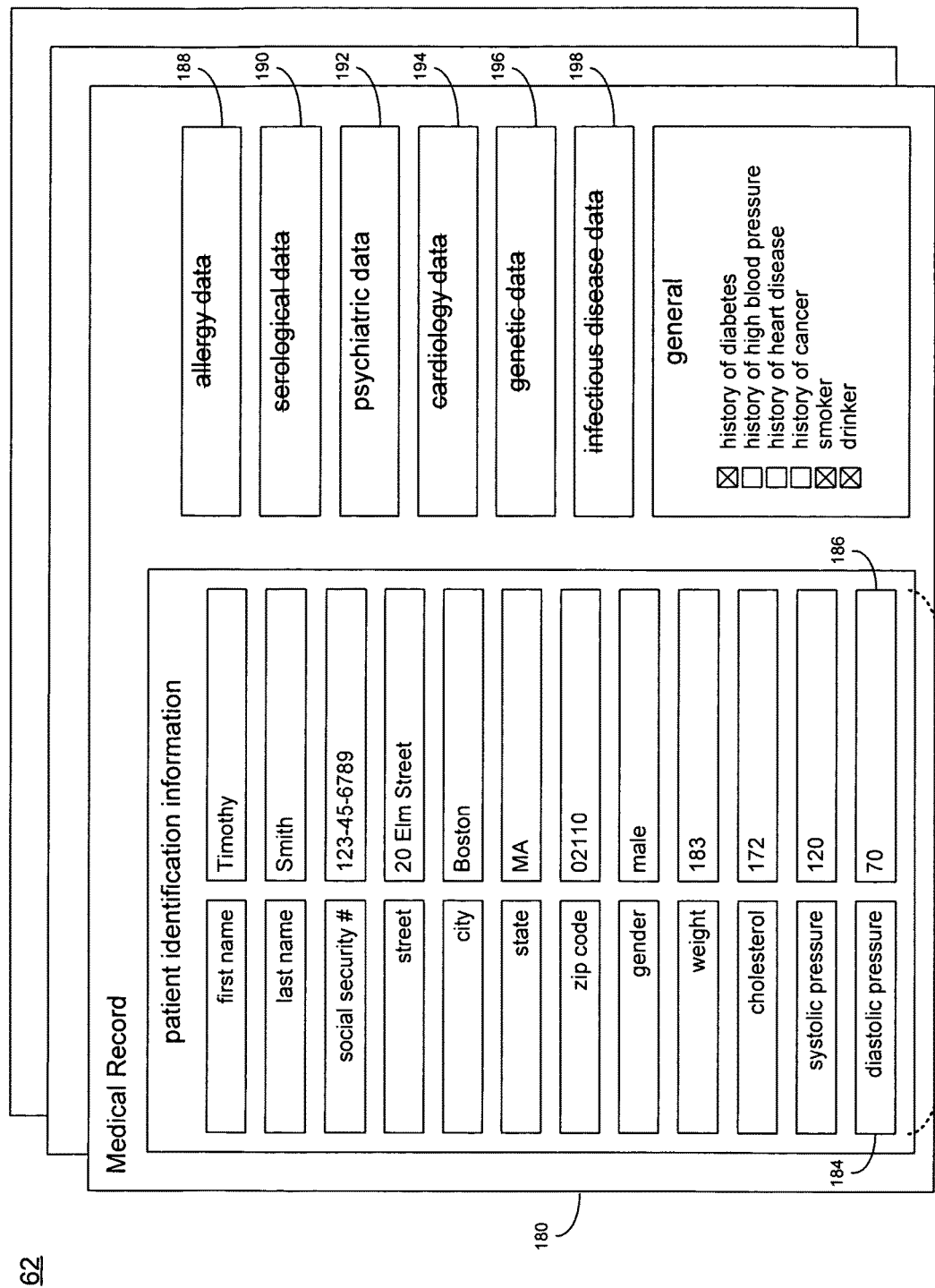
FIG. 7 is a diagrammatic view of a patient's medical record rendered by the record organization system of FIG. 1

Referring also to FIG. 7, medical record 62 may be displayed in a separate window or displayed full screen on the display of client computer 34. As discussed above, the key provided to the medical service provider 18 only allows access to the portion(s) of the patient's medical record that the patient wishes to allow access. As discussed above, Timothy Smith (i.e., patient 22) is being treated by medical service provider 18 for depression and access key 14 grants access to the general and psychiatric portions of Timothy Smith's medical record.

However, access key 14 does not permit access (i.e., prohibits access) to the other portions of Timothy Smith's medical record, namely Allergies, Serological Data, Cardiology Data, Genetic Data, and Infectious Disease Data. Accordingly, these portions of the patient's medical record are unavailable.

Medical records (e.g., medical record 62) are typically database records 180 that define general patient data through the use of various data fields (e.g., data field 182), each of which includes a field name 184 and a field value 186. Field value 186 may define an amount (e.g., a patient's systolic pressure) or a binary condition (e.g., whether or not a patient is a smoker). Additionally, as discussed above, the medical records include allergy data 188, serological data 190, psychiatric data 192, cardiology data 194, genetic data 196, and infectious disease data 198, each of which may be further broken down into data fields.

Through the use of record processing module 58, the medical service provider 18 may configure record organization system 10 so that selected data fields (e.g., data field 182) within a patient's medical record (e.g., medical record 62) may be automatically populated with desired field data obtained from the patient/trusted third party (e.g., a spouse, parent, or private nurse, for example), herein after a data source.

Referring again to FIG. 5, if a patient has a condition that requires medical supervision, it may be desirable for the medical service provider to define certain data fields within the medical record of that patient as data fields that need to be populated in the future, either on a one-time or a recurring basis.

For example, if a patient is seeing a medical service provider for treatment of hypertension, it may be desirable for the medical service provider to update the medical record of the patient to include weekly systolic and diastolic blood pressure readings. Further, if a patient is seeing a medical service provider for dietary reasons and the medical service provider places that patient on a diet, it may be desirable to update the medical record of the patient to include weekly or monthly weight measurements.

Accordingly, if desired (as may be determined in operational block 144 of FIG. 5), record processing module 58 allows the medical service provider 18 to define 146 one or more data fields (e.g., data field 182) within a patient's medical record for which desired field data (e.g., the patient's diastolic pressure) is to be acquired. When defining the data field(s) to be automatically populated/updated, the medical service provider may define the populate/update procedure as a one-time event, or a recurring event. For example, the medical service provider may only be interested in obtaining the weight of a patient once (e.g., three months after the start of a diet). However, if a patient is suffering from chronic hypertension, the medical service provider may be interested in obtaining blood pressure readings on a monthly, weekly, or daily basis. Accordingly, when defining 146 the data field(s) for which field data is to be obtained, the date, time, and frequency of the event is also defined.

Once the field(s) are properly defined, at the scheduled date and time, the data source is contacted 148. Contacting the data source may include transmitting 150 an email or other electronic message to the data source, and providing 152 the data source with text-based instructions concerning responding. Alternatively, the data source may be contacted telephonically 154, and provided 156 with speech-based instructions concerning responding.

Examples of these instructions include a text or speech-based greeting such as "Hello, this is the Family Medical Clinic. We are calling to obtain your latest diastolic blood pressure reading".

Once initial contact is made with the data source, the data source is authenticated 158 (to confirm the identity of the data source), such that the authentication method varies depending on the type of contact made with the data source.

If the data source was contacted via email, the authentication process may require the data source to transmit 160 a password or PIN (i.e., personal identification number), which is subsequently received 162 by the medical service provider. This password or PIN may be included in the email response that the data source provides to the medical service provider. Alternatively, the data source may be required to provide 164 a digital certificate with their email response, which is subsequently received 166 by the medical service provider.

As is known in the art, a digital certificate is a file that identifies the user (i.e., in this situation, the data source) and include a copy of the user's public encryption key.

If the data source was contacted via the telephone, the authentication process may require that the data source enter 168 a password or PIN, which is subsequently received 170 by the medical service provider. Entry of the password/PIN may be accomplished through the use of the keypad on the patient's telephone. Alternatively, a verbal password/PIN may be used, in which the data source speaks 172 the password/PIN and voice recognition software (not shown) incorporated into the record organization system 10 receives 174 and analyzes the data source's spoken word to provide authentication.

Once authenticated, the data source enters and transmits the desired field data, which is subsequently received 176 by record processing module 58. Again, the manner in which the data source enters and transmits the desired field data varies depending on the manner in which the data source was contacted. As above, the desired field data may be incorporated into an email, spoken into the telephone, or entered into the telephone via the telephone keypad. Once received, the desired field data is used to update 178 the medical record of the patient. This updating procedure may overwrite the old field data, or may enter the new field data as a chronological entry, thus allowing for historical tracking of the field data.

While the centralized key repository 50 and the centralized medical record repository 52 are described above as being located on a remote server, other configurations are possible. For example, as is known in the art, one or more of these repositories may be distributed across multiple computers/servers.

A number of implementations have been described. Nevertheless, it will be understood that various modifications may be made. Accordingly, other implementations are within the scope of the following claims.

What is claimed is:

1. A method for facilitating data entry and secure data access via a web-enabled application using a record organization system including a key processing module, a key maintenance module and a record processing module comprising:
   in a computer-based medical record including a plurality of data fields, defining, using the record processing module, one or more data fields for which desired field data is to be acquired;
   accessing, by a patient associated with the computer-based medical records, the record organization system via the web-enabled application using an encrypted connection;
   rendering, by the key maintenance module of the record organization system, a screen display including an individually selectable listing of each of the plurality of data fields, whereby the patient associated with the computer-based medical records selects one or more of the individually selectable plurality of data fields and assigns a defined first access level thereto;
   receiving by the record organization system from the patient associated with the computer-based medical record a request to assign the defined first access level to a first medical provider;
   encrypting, by the key maintenance module, access to the one or more selected data fields assigned to the first access level;
   generating, by the key maintenance module, a first individual access key for the first access level, whereby the first individual access key is used to decrypt and provide access to the one or more selected data fields assigned to the first access level;
   receiving by the first medical service provider a copy of the first individual access key;
   receiving the first individual access key at the key processing module, associating the first individual access key with the first medical service provider and storing the first individual access key therein;
   automatically populating by the record processing module at least one of the one or more data fields with desired field data from a data source, said automatically populating comprising:
      receiving, by the record processing module that is stored to a computer-readable medium and executing on a processor-based computer, a schedule for contacting said data source to prompt said data source for the desired field data for said at least one data field;
      triggering, by said record processing module, contacting said data source in possession of the desired field data in accordance with said schedule; and
      receiving, by said record processing module, the desired field data from the data source; and
   accessing, by the first medical service provider, the record organization system via the web-enabled application using an encrypted connection;
   rendering, by the record processing module of the record organization system, a screen display upon access thereto by the first medical service provider, the rendered screen display including an individually selectable list of patients who have provided the first medical service provider with access to one or more data fields within the patients' computer based medical record;
   receiving by the record processing module of the record organization system from the first medical service provider, a selection of the patient, retrieving by the record processing module the first individual access key, decrypting access to the one or more selected data fields assigned to the first access level using the first individual access key and granting access to the first medical provider to the selected one or more data fields associated with the first access level.

2. The method of claim 1, further comprising updating, by said record processing module, the computer-based medical record to include the received desired field data.

3. The method of claim 1, wherein the data source is the patient and the medical record defines at least a portion of the medical history of the patient.

4. The method of claim 1, wherein contacting a data source includes authenticating the data source.

5. The method of claim 4, wherein authenticating the data source includes:
   requiring that the data source enter an electronic password; and
   receiving the electronic password.

6. The method of claim 4, wherein authenticating the data source includes:
   requiring that the data source speak a verbal password; and
   receiving the verbal password.

7. The method of claim 4, wherein authenticating the data source includes:
   requiring that the data source provide an authenticating digital certificate; and
   receiving the authenticating digital certificate.

8. The method of claim 1, wherein contacting a data source includes transmitting an email to the data source.

9. The method of claim 8, wherein contacting a data source further includes providing the data source with text-based instructions concerning the desired field data.

10. The method of claim 1, wherein contacting a data source includes telephonically contacting the data source.

11. The method of claim 10, wherein contacting a data source includes providing the data source with speech-based instructions concerning the desired field data.

12. The method of claim 1, wherein the desired field data concerns a numeric range-based variable that can accept any numeric value within a range of valid numeric values.

\* \* \* \* \*